United States Patent [19]

Sugahara et al.

[11] Patent Number: 5,534,251

[45] Date of Patent: Jul. 9, 1996

[54] STABILIZED IL-1α MEDICINAL COMPOSITION

[75] Inventors: Yuji Sugahara; Yasuo Nakayama, both of Tokushima, Japan

[73] Assignee: Otsuka Pharmaceutical Co., Ltd., Tokyo, Japan

[21] Appl. No.: 193,182

[22] PCT Filed: Jul. 31, 1992

[86] PCT No.: PCT/JP92/00983

§ 371 Date: Feb. 14, 1994

§ 102(e) Date: Feb. 14, 1994

[87] PCT Pub. No.: WO93/03747

PCT Pub. Date: Mar. 4, 1993

[30] Foreign Application Priority Data

Aug. 12, 1991 [JP] Japan ................................. 3-201702

[51] Int. Cl.$^6$ .................................................. A61K 45/05
[52] U.S. Cl. .................. 424/85.2; 530/351; 530/363; 514/12
[58] Field of Search ................ 424/85.2; 530/351, 530/363; 514/12

[56] References Cited

U.S. PATENT DOCUMENTS 4,816,436  3/1989  Jacobs ........................... 514/2
5,120,534  6/1992  Hirai et al. ..................... 424/85.2

FOREIGN PATENT DOCUMENTS

| 0229016 | 7/1987 | European Pat. Off. . |
| 0391444 | 10/1990 | European Pat. Off. . |
| 2292726 | 12/1987 | Japan . |
| 3164899 | 8/1988 | Japan . |
| 2138222 | 5/1990 | Japan . |
| 2157231 | 6/1990 | Japan . |
| 3236328 | 10/1991 | Japan . |
| 9116916 | 11/1991 | WIPO . |

OTHER PUBLICATIONS

Wang et al., J. Parenteral Sci & Tech., vol. 42 (2S), pp. 53–526, 1988.
Hamblin, "Lymphokines", IRL Press, pp. 19–20, 1988.
Dinarello, The FASEB Journal, vol. 2, pp. 108–115, 1988.

*Primary Examiner*—Chhaya D. Sayala
*Attorney, Agent, or Firm*—Sughrue, Mion, Zinn, Macpeak & Seas

[57] ABSTRACT

The invention provides a stabilized IL-1α medicinal composition comprising an IL-1α active substance, serum albumin and a saccharide. The medicinal composition of the invention has very desirable characteristics in terms of the stability of its active ingredient IL-1α active substance, rendering it stable throughout its processing into various dosage forms, such as freezing and freeze-drying, and for a long time after production under the usual storage conditions, thus being of great utility value in the relevant field.

6 Claims, No Drawings

STABILIZED IL-1α MEDICINAL COMPOSITION

TECHNICAL FIELD

The present invention relates to a novel stabilized medicinal composition of an interleukin-1α (IL-1α) active substance.

PRIOR ART AND ITS PROBLEMS

The resolution was passed at the Second International Lymphokine Workshop that the physiologically active substance reported earlier under the varied names of lymphocyte activating factor (LAF), mitogenic protein, helper peak-1, T-cell replacing factor III (TRF-III) or T-cell replacing factor Me (TRFM), B-cell activating factor, B-cell differentiation factor, etc. should thenceforth be referred to by the unified designation of interleukin-1 (IL-1) [Cellular Immunol., 48, 433–436 (1979)]. This decision was based on the reasoning that these bioactive substances cannot be discriminated as different chemical entities but were merely so designated with attention paid to various aspects of physiological activity.

IL-1, mentioned above, has been reported to activate T- and B-lymphocytes, enhances the production of interleukin-2 (IL-2) and antibodies, acts on the hepatocytes to encourage protein synthesis and increases the production of prostaglandins [cf. Reviews of Infectious Disease, Vol. 6, No. 1, 51–59 (1984), New England J. of Med., 311, 1413 (1984), etc.]. More recently, the existence of genes coding for polypeptides having LAF activity or their precursors have been reported [Proc. Natl. Acad. Sci., 81, 7907–7911 (1984); Nature, 315, 641 (1985); Nucleic Acids Research, 13 (16) 5869 (1985)] and a polypeptide having the amino acid sequence designated as SEQ ID NO:1 in the sequence listing presented hereinafter came to be known as IL-1α.

The inventors of the present invention, who also made an intensive exploration into IL-1α as a homogeneous or discrete substance, already established a production technology for the substance and elucidated its characteristics as a chemical entity as well as its physiological activities. Based on the research findings so generated, the inventors found, too, that a polypeptide which can be designated by the amino acid sequence given in the sequence listing presented hereinafter has LAF activity but that despite its correspondence to physiologic genes as reported, this peptide was a labile substance. Meanwhile, it was known that the administration of IL-1α as a drug to human subjects entails the onset of fewer as a side effect and this was found to be a serious drawback in the medicinal application of IL-1α.

As the result of further investigations, the inventors of the present invention succeeded in providing a new IL-1α derivative differing from said IL-1α in amino acid sequence, which is definitely free from pyrogenicity and particularly suited for medicinal uses [cf. Japanese Patent Application Kokai S63-164899 and Kokai H2-167298].

The above IL-1α derivative has a variety of activities such as LAF activity, tumor growth inhibitory activity (activity to specifically inhibit the growth of tumor cells), activity to enhance the production of various cytokines such as CSF (colony stimulating factor), interferons (IFN), interleukin-2 (IL-2), interleukin-3 (IL-3), etc. (an action, for example, on human cells to significantly enhance the production of said cytokines), antiinflammatory activity (particularly the activity to effectively arrest the progression of arthritis in animal models of arthritis), radiation hazard preventing effect (the property to prevent or inhibit tissue damages and serious side effects associated with systemic radiotherapy in bone marrow transplantation, radiotherapy for cancer or accidental exposure to radiation), antithrombotic effect, platelet increasing effect (blood increasing effect), etc. and is of value as a drug, namely an immunopotentiator for the promotion of antibody production, potentiation of vaccines, etc., an antitumor agent, a stimulant for enhanced production of cytokines such as CSF, IL-2, IL-3, etc., an antiinflammatory agent, a radiation injury protectant, an antithrombotic agent, a therapeutic agent for thrombocytopenia and so on. Moreover, this derivative has characteristically a low toxic potential and less pyrogenic than the conventional IL-1α, suggesting that it is a highly safe medicinal substance.

However, in the application of a substance as a drug, it is essential that its activity remain stable without aging in ordinary pharmaceutical dosage forms and under the usual storage conditions. These requirements apply, of course, to said IL-1α derivative and particularly in a homogeneous preparation purified to a degree permitting clinical application, sufficient care is required in handling from stability points of view, viz. for upholding its intrinsic activity. However, as far as IL-1α and its derivatives are concerned, no research and development work has been done in the aspect of performance requirements for medical use and the development of an improved stable medicinal composition which would remain stable under freezing or freeze-drying conditions and various storage time and temperature conditions has been earnestly awaited by the industry.

The object of the present invention is to overcome the above disadvantages and provide a stabilized medicinal composition of an IL-1α active substance which is particularly suited for use as a pharmaceutical product.

DISCLOSURE OF INVENTION

The inventors of the present invention found after much research with the above object in mind that when a IL-1α derivative defined hereinafter as the IL-1α active substance is selected, formulated with specified amounts of human serum albumin and sucrose and adjusted to a neutral pH range with a buffer solution, the activity of said IL-1α active substance is remarkably stabilized. The present invention is based on the above finding.

In accordance with the present invention there is provided a stabilized medicinal composition of IL-1α characterized by containing the following ingredients (1)–(3) and having been adjusted to a neutral range with a buffer solution.

(1) a pharmacologically effective amount of a human IL-1α derivative having an amino acid sequence corresponding to the amino acid sequence designated by SEQ ID NO:1 in which Asn in 36-position has been replaced with Asp and Cys in 141-position replaced with Ser, (2) serum albumin, and (3) a saccharide.

This IL-1α derivative, as the IL-1α active substance to be utilized as the active ingredient of the medicinal composition according to the present invention, is characterized in that its amino acid sequence corresponds to human IL-1α having the amino acid sequence shown as SEQ ID NO:1 in which Asn in 36-position has been replaced with Asp and Cys in 141-position replaced with Ser.

The nomenclature of amino acids and polypeptides as used throughout this specification is in accordance with the abbreviations and rules of IUPAC and IUPAC-IUB or the abbreviations used commonly in this field for amino acid residues. Moreover, the number and positions of amino acid residues correspond to those of the amino acid sequence shown in the above-mentioned sequence listing even if there are defections.

The above-mentioned IL-1α derivative can be produced, for example by inserting a gene coding for the amino acid sequence shown as SEQ ID NO:1 in the sequence listing given hereinafter, or a modified amino sequence thereof, into a microbial vector for replication, transcription and translation in the microbial cell. [Japanese Patent Application Kokai S63-164899 and H2- 167298].

The medicinal composition of the present invention is now described in detail. This medicinal composition essentially comprises a pharmacologically effective amount of said IL-1α derivative (IL-1α active substance), serum albumin and a saccharide and has been adjusted to a neutral pH range with a buffer solution.

The pharmacologically effective amount of IL-1α derivative is well known to those skilled in the art and there is no particular limitation. Generally, however, the dose can be advantageously selected from the range of about 0.001–100 μg and preferably about 0.1–10 μg.

The serum albumin is preferably human serum albumin and the saccharide is preferably sucrose but these are not exclusive choices and other ordinary serum albumins and saccharides can be employed.

The proper level of addition of said serum albumin is not less than about 0.1 mg, preferably about 1–10 mg, based on the medicinal composition (1 ml), and that of said saccharide is about 1–100 mg, preferably about 3–10 mg, based on the composition (1 ml).

As to the buffer solution, there is no particular limitation only if the composition is controlled within the neutral range. For example, buffer solutions containing phosphate, titrate or other salts can be used with advantage. Particularly preferred is 0.01M sodium phosphate-disodium phosphate buffer. The term 'neutral range' in the context of the invention means a range of about pH 6–8, preferably about 6.5–7.5.

The medicinal composition of the invention can be similar to ordinary medicinal compositions of this kind except for the above-mentioned essential requirements and may contain other pharmacologically active substances and ordinary pharmaceutical additives in optional proportions. As such other ingredients that can be contained in the medicinal composition of the invention may be mentioned usual surfactants such as polyethylene glycol sorbitan alkyl esters, polyoxyethylene alkyl ethers, sorbitan monoacyl esters, fatty acid glycerides, sulfur-containing reducing agents such as cysteine, N-acetylhomocysteine, thioctic acid, thioglycolic acid and their salts, thioethanolamine, thioglycerol, sodium thiosulfate, thiolactic acid, dithiothreitol, glutathione, etc. and amino acids such as glycine and so on.

The medicinal composition of the invention is advantageously isotonized with a conventional isotonizing agent to provide a stable isotonic preparation. Typical examples of the isotonizing agent that can be used are salts such as sodium chloride and amino acids such as glycine.

The medicinal composition of the present invention can be further formulated with suitable pharmaceutical carriers to provide various dosage forms. Those pharmaceutical carries which are commonly used in the production of pharmaceutical preparations according to the intended dosage form are all usable. Thus usable as excipients or diluents are fillers, extenders, binders, humectants, disintegrants and so on. The form of the pharmaceutical composition is not particularly limited insofar as it contains an IL-1α active substance, for example, solid forms such as tablets, powders, granules and pills and injectable liquid forms such as solutions, suspensions and emulsions. Furthermore, said composition can be in the form of a dried product, which can be rendered liquid by addition of an appropriate vehicle prior to use. These pharmaceutical dosage forms can be prepared by the conventional methods.

The pharmaceutical preparation thus obtained can be administered via an appropriate route selected according to the particular dosage form. When it is in the form of an injection, for instance, the pharmaceutical preparation can be administered intravenously, intramuscularly, subcutaneously, intradermally or intraperitoneally, for instance. When in a solid form, the pharmaceutical preparation can be administered orally or enterally. The content of the active ingredient in the pharmaceutical preparation and the amount of the preparation may vary according to the method of administration, specific dosage form, the object of use, the condition of the patient to whom the preparation is applied, and other factors. Generally, however, it is desirable that a preparation containing the active ingredient in an amount ranging from about 0.0000001 to 80% by weight be prepared and that this preparation be administered in a daily dose, calculated as the active ingredient contained therein, of about 0.001 to 100 μg per human adult. This daily dose need not be given as a single dose but may be administered in three or four divided doses.

By taking advantage of the various physiological activities of its active ingredient IL-1α derivative, such as LAF activity, activity to inhibit the growth of tumor cells (GIF activity), i.e. activity to specifically inhibit the growth of tumor cells, activity to promote the production of various cytokines such as CSF, IFN, IL-2 and IL-3, i.e. an action, for example, on human cells to markedly enhance the production of such cytokines, antiinflammatory activity, e.g. activity to effectively inhibit the progression of arthritis in animal models of arthritis, and activity to prevent radiation injury, i.e. activity to prevent tissue damages and serious side effects that would result from systemic irradiation during bone marrow transplantation, radiotherapy of cancer or accidental exposure to radiation, the medicinal composition of the present invention is of great use as an immune system stimulant, for example for promoting the production of antibodies and potentiating the effect of vaccines, an antitumor agent, an agent for promoting the production of cytokines such as CSF, IL-2 and IL-3, an antiinflammatory agent, an agent for preventing radiation injury, an antithrombotic drug, a therapeutic agent for thromocytopenia, or other medicinal agent. The medicinal composition of the invention is effective especially as a CSF production promoting agent. For example, when administered to man, the composition effectively cures granulocytopenia due to impaired formation of bone marrow resulting from chemotherapy or radiation therapy for cancers without entailing the risk of virus infections or antigen-antibody reactions (a therapeutic agent for granulocytopenia). The CSF production promoting preparation is usable also for preventing and curing various diseases utilizing the activity of CSF the production of which is promoted by the agent so administered. For example, CSF acts to enhance the function of granulocytes and macrophages (Lopez, A. F. et al., J. Immunol., 131, 2983 (1983); Handam, E. et al., ditto, 122, 1134 (1979) and Vadas, M. A. et al., ditto, 130, 795 (1983), so that clinical application is expected of CSF for preventing and curing various infections. Accordingly, this CSF production promoting preparation is expected to be clinically useful. The medicinal composition of the invention is effective also for preventing and curing opportunistic infections which occur frequently especially when anticancer drugs are given. For example, they are useful for preventing and curing various infections which develop during chemotherapy of acute leukemia and in bone marrow transplantation, such as candidiasis, cryptococcosis, aspergillosis, zygomycosis, chromomycosis, viral infections, Cytomegalovirus pneumonia and complications of these infections.

In accordance with the present invention there is provided a stabilized pharmaceutical formula for IL-1α active substances which are the focus of much attention and expectation. The resulting medicinal composition of the invention has very desirable characteristics in terms of the stability of its active ingredient IL-1α active substance, rendering it stable throughout its processing into various dosage forms, such as freezing and freeze-drying, and for a long time after production under the usual storage conditions, thus being of great utility value in the relevant field.

BEST MODE FOR PRACTICING THE INVENTION

The following examples are intended to describe the invention in further detail. The IL-1α-active substance (IL-1α derivative) used as the active ingredient in each example was disclosed in Japanese Patent Application Kokai S63-164899 and H2-167298 and is herein designated briefly as [$Asp^{36}$] [$Ser^{141}$] IL-1α.

EXAMPLE 1

Buffer salt solutions each containing 1 μg of [$Asp^{36}$] [$Ser^{141}$] IL-1α and 0.1 mg of human serum albumin in each milliliter and having the pH value indicated below in Table 1 were prepared.

These compositions were respectively allowed to stand in glass vials (air-tight, protected from light) at 37° C. for 3 days and the residual amount of the IL-1α -active substance (%) in each sample was determined by high performance liquid chromatography (HPLC; Tosoh HPLC system) under the following conditions.

Column: Nucleosil 5C18 (4.6 ⌀×2.50 mm; GL Science Inc.)
Solvents: A=0.1% TFA-H$_2$O
B=0.1% TFA (acetonitrile:water=9:1, v/v)

| Gradient program | Time (min.) | B, % |
| --- | --- | --- |
| | 0 | 35 |
| | 10 | 47 |
| | 55 | 50 |
| | 60 | 100 |
| | 65 | 100 |
| | 70 | 35 |

Detection: Ultraviolet absorption (220 nm)
The results are shown in Table 1.

TABLE 1

| Sample No. | Buffer solution | % Residue after 3 days at 37° C. |
| --- | --- | --- |
| 1 | 0.01M Citric acid-sodium citrate (pH 5.0) | 60.6 |
| 2 | 0.01M Citric acid-sodium citrate (pH 6.0) | 86.0 |
| 3 | 0.01M Monosodium phosphate-disodium phosphate (pH 7.0) | 89.1 |

TABLE 1-continued

| Sample No. | Buffer solution | % Residue after 3 days at 37° C. |
| --- | --- | --- |
| 4 | 0.01M Monosodium phosphate-disodium phosphate (pH 8.0) | 83.8 |

In Table 1, the residue (%) is the value calculated with the amount of the active ingredient immediately after formulation being taken as 100%.

It is clear from Table 1 that [$Asp^{36}$][$Ser^{141}$] IL-1α can be stabilized by maintaining it in the neutral range of pH 6–8 and particularly at pH 7.

EXAMPLE 2

0.01M monosodium phosphate-disodium phosphate buffer solutions (pH 7) each containing 1 μg of [$Asp^{36}$][$Ser^{141}$] IL-1α, a varying amount of human serum albumin as indicated in Table 2 and 0.01 mg of Tween 80 in each milliliter were prepared.

The above compositions were respectively lyophilized and stored in glass vials (air-tight, protected from light) at 40° C. for one week. After reconstitution with water, the amount of IL-1α-active substance immediately after lyophilization and that after 1 week of storage were determined in the same manner as Example 1. The results are shown in Table 2.

TABLE 2

| | | Residue (%) | |
| --- | --- | --- | --- |
| Sample No. | Amount of HSA (mg) | Immediately after lyophilization | After 1 week at 40° C. |
| 1 | — (Not added) | 53.5 | 19.3 |
| 2 | 0.01 | 88.1 | 52.4 |
| 3 | 0.1 | 95.5 | 79.3 |
| 4 | 1 | 98.7 | 90.7 |

The residue (%) in Table 2 is the value calculated with the amount of the active ingredient prior to lyophilization being taken as 100%.

It can be seen from Table 2 that [$Asp^{36}$][$Ser^{141}$] IL-1α can be stabilized by adding about 0.1 mg or more of human serum albumin per 1 μg of the derivative.

EXAMPLE 3

0.01M Monosodium phosphate-disodium phosphate buffer salt solutions (pH 7) each containing 1 μg of [$Asp^{36}$] [$Ser^{141}$] IL-1α, 0.1 mg of human serum albumin and one of the additives mentioned at the level indicated in Table 3 in each milliliter were prepared.

Each of the resultant compositions was lyophilized and stored in glass vials (air-tight, protected from light) at 40° C. for 4 weeks and after reconstitution with water the amount (%) of IL-1α-active substance immediately after lyophilization and that after 4 weeks of storage were determined as in Example 1. The results are shown in Table 3.

TABLE 3

| Sample No. | Additive | | Residue (%) Immediately after lyophilization | After 4 weeks at 40° C. |
|---|---|---|---|---|
| 1 | — | (Not added) | 89.6 | 59.7 |
| 2 | Maltose | 5 mg | 86.4 | 35.2 |
| 3 | Mannitol | 5 mg | 96.0 | 62.1 |
| 4 | Glycine | 5 mg | 91.4 | 75.6 |
| 5 | Dextran 40 | 5 mg | 86.6 | 59.4 |
| 6 | Sucrose | 5 mg | 91.2 | 89.1 |
| 7 | NaCl | 8.3 mg | 96.2 | 58.7 |

The residue (%) in Table 3 is the value calculated with the amount of the active ingredient prior to lyophilization being taken as 100%.

It can be seen from Table 3 that [Asp$^{36}$][Ser$^{141}$] IL-1α can be remarkably stabilized by the addition of sucrose as chosen from among the various saccharides, amino acid and salt.

EXAMPLE 4

0.01M Monosodium phosphate-disodium phosphate buffer solutions (pH 7) each containing 1 µg of [Asp$^{36}$][Ser$^{141}$] IL-1α, 1 mg of human serum albumin, 5 mg of sucrose and one of the various isotonizing agents at the level indicated in Table 4 in each milliliter were prepared to provide stabilized pharmaceutical compositions of the invention. Sample No. 1 is a control composition not containing sucrose, 5 mg, but otherwise identical (no isotonizing agent).

Each of the above compositions was lyophilized and stored in glass vials (air-tight, protected from light) at 40° C. for 4 weeks and after reconstitution with water the amount (%) of the IL-1α-active substance immediately after lyophilization and that after 4 weeks of storage were determined as in Example 1. The results are shown in Table 4.

TABLE 4

| Sample No. | Isotonizing agent | | Residue (%) Immediately after lyophilization | After 4 weeks at 40° C. |
|---|---|---|---|---|
| 1 | (No sucrose), control | | 97.7 | 81.2 |
| 2 | No additive | | 101.3 | 96.1 |
| 3 | Glycine | 19.2 mg | 97.8 | 87.5 |
| 4 | NaCl | 7.9 mg | 101.5 | 93.2 |

The residue (%) in Table 4 is the value calculated with the amount prior to lyophilization being taken as 100%.

It is clear from Table 4 that Samples No. 2, 3 and 4, which are pharmaceutical compositions of the invention, are very stable IL-1α preparations.

The above examples indicate that the pharmaceutical composition of the invention is excellent in stability.

---

We claim:

1. A stabilized IL-1α medicinal composition consisting essentially of the following ingredients (1)–(3), adjusted to a pH of 7 with a buffer solution:
   (1) a pharmacologically effective amount of a human IL-1α derivative having an amino acid sequence designated by SEQ ID NO: 1 in which 36-Asn is replaced with Asp and 141-Cys is replaced with Ser,
   (2) about 1–10 mg per milliliter of human serum albumin, and
   (3) about 3–10 mg per milliliter of sucrose.

2. The stabilized medicinal composition of claim 1 wherein said buffer solution is 0.01M monosodium phosphate-disodium phosphate buffer.

3. The stabilized medicinal composition of claim 1 wherein said buffer is 0.01M monosodium phosphate-disodium phosphate buffer and which contains about 1 mg of human serum albumin and about 5 mg of sucrose in each milliliter.

4. The stabilized medicinal composition of claim 1 wherein the pharmacologically effective amount of human IL-1α derivative is about 0.001–100 μg per milliliter of the composition.

5. The stabilized medicinal composition of claim 4 wherein the pharmacologically effective amount of human IL-1α derivative is about 0.1–10 μg per milliliter of the composition.

6. The stabilized medicinal composition of claim 1 which is a frozen or lyophilized form.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ser  Ala  Pro  Phe  Ser  Phe  Leu  Ser  Asn  Val  Lys  Tyr  Asn  Phe  Met  Arg
 1                 5                      10                          15
Ile  Ile  Lys  Tyr  Glu  Phe  Ile  Leu  Asn  Asp  Ala  Leu  Asn  Gln  Ser  Ile
               20                     25                      30
Ile  Arg  Ala  Asn  Asp  Gln  Tyr  Leu  Thr  Ala  Ala  Ala  Leu  His  Asn  Leu
          35                          40                 45
Asp  Glu  Ala  Val  Lys  Phe  Asp  Met  Gly  Ala  Tyr  Lys  Ser  Ser  Lys  Asp
     50                          55                      60
Asp  Ala  Lys  Ile  Thr  Val  Ile  Leu  Arg  Ile  Ser  Lys  Thr  Gln  Leu  Tyr
65                      70                      75                          80
Val  Thr  Ala  Gln  Asp  Glu  Asp  Gln  Pro  Val  Leu  Leu  Lys  Glu  Met  Pro
                    85                      90                      95
Glu  ILe  Pro  Lys  Thr  ILe  Thr  Gly  Ser  Glu  Thr  Asn  Leu  Leu  Phe  Phe
               100                     105                     110
Trp  Glu  Thr  His  Gly  Thr  Lys  Asn  Tyr  Phe  Thr  Ser  Val  Ala  His  Pro
          115                     120                     125
```

| | | | | | | | | | | | | | | |
|---|---|---|---|---|---|---|---|---|---|---|---|---|---|---|
| Asn | Leu | Phe | Ile | Ala | Thr | Lys | Gln | Asp | Tyr | Trp | Val | Cys | Leu | Ala | Gly |
| | 130 | | | | | 135 | | | | | 140 | | | | |
| Gly | Pro | Pro | Ser | Ile | Thr | Asp | Phe | Gln | Ile | Leu | Glu | Asn | Gln | Ala |
| 145 | | | | | 150 | | | | | 155 | | | | |